(12) United States Patent
Mallick et al.

(10) Patent No.: US 8,623,394 B2
(45) Date of Patent: Jan. 7, 2014

(54) IMPLANT FOR TISSUE ENGINEERING

(75) Inventors: Kajal K. Mallick, Coventry (GB); James O. Meredith, Glos (GB)

(73) Assignee: The University of Warwick, Coventry (GB)

( * ) Notice: Subject to any disclaimer, the term of this patent is extended or adjusted under 35 U.S.C. 154(b) by 952 days.

(21) Appl. No.: 12/298,618

(22) PCT Filed: Apr. 25, 2007

(86) PCT No.: PCT/GB2007/001520
§ 371 (c)(1),
(2), (4) Date: Oct. 27, 2008

(87) PCT Pub. No.: WO2007/125323
PCT Pub. Date: Nov. 8, 2007

(65) Prior Publication Data
US 2009/0155334 A1 Jun. 18, 2009

(30) Foreign Application Priority Data
Apr. 27, 2006 (GB) .................................. 0608345.5

(51) Int. Cl.
*A61F 13/00* (2006.01)
(52) U.S. Cl.
USPC ........................................................ 424/422
(58) Field of Classification Search
None
See application file for complete search history.

(56) References Cited

U.S. PATENT DOCUMENTS

| | | | |
|---|---|---|---|
| 5,237,158 A | 8/1993 | Kern et al. | |
| 5,240,659 A | 8/1993 | Ichitsuka et al. | |
| 5,370,681 A | 12/1994 | Herweck et al. | |
| 6,730,252 B1 * | 5/2004 | Teoh et al. | 264/178 F |
| 2004/0024081 A1 * | 2/2004 | Trieu et al. | 523/113 |

FOREIGN PATENT DOCUMENTS

| | | |
|---|---|---|
| GB | 2 209 000 | 4/1989 |
| WO | WO 2004/105824 | 12/2004 |
| WO | WO 2005/004263 | 1/2005 |

OTHER PUBLICATIONS

Avila, et al. "Monolithic Reactors for Environmental Applications: A Review on Preparation Technologies." Chemical Engineering Journal 109: 11-36 (2005).
Buser, et al. "Influence of Surface Characteristics on Bone Integration of Titanium Implants: A Histomorphometric Study in Miniature Pigs." Journal of Biomedical Materials Research 25(7): 889-902 (Jul. 1991).
Compston "Understanding Osteoporosis" Family Doctor Series (1998).
Erbe, et al. "Potential of an Ultraporous β-tricalcium Phosphate Synthetic Cancellous Bone Void Filler and Bone Marrow Aspirate Composite Graft." Eur Spine Journal 10: S141-S146 (2001).
Forzatti, et al. "Preparation and Characterization of Extruded Monolithic Ceramic Catalysts." Catalysis Today 41: 87-94 (1998).
Kieswetter, et al. "The Role of Implant Surface Characteristics in the Healing of Bone." Critical Reviews in Oral Biology & Medicine 7(4): 329-345 (1996).
Nordin and Frankel *Basic Biomechanics of the Musculoskeletal System* ($2^{nd}$ Ed.) Chapter 5: "Biomechanics of Skeletal Muscle." pp. 89-109 (1989).
Petite, et al. "Tissue-Engineered Bone Regeneration." Nature Biotechnology 18: 959-963 (2000).
Porter, et al. "Mechanical Propertiesf a Biodegradable Bone Regeneration Scaffold." Journal of Biomechanical Engineering 122(3): 286-288 (2000).
Spence *Basic Human Anatomy* ($3^{rd}$ Ed.) Chapter 4: "The Integumentary System." pp. 77-91 (1990).
de Sousa and Evans "Tubular Hydroxyapatite Scaffolds." Advances in Applied Ceramics 104(1): 30-34 (2005).
Yaxiong, et al. "The Customized Mandible Substitute Based on Rapid Prototyping." Rapid Prototyping Journal 9(3): 167-174 (2003).
"Laboratory of Environmental Catalysis. Boreskov Institute of Catalysis, Department of Environmental Catalysis." downloaded from the Internet on Aug. 19, 2009.
Cross-Section of Femur BA216 from Medical Art Service. downloaded from the Internet on Jan. 27, 2009.

* cited by examiner

*Primary Examiner* — Allison Ford
*Assistant Examiner* — Yvonne Pyla
(74) *Attorney, Agent, or Firm* — Hunton & Williams LLP (57) ABSTRACT

The invention provides a process for the production of a monolithic implant for use in tissue engineering, the process comprising the steps of plasticizing at least one biocompatible material into a paste, extruding the paste through a die, and drying the extruded material to eliminate an aqueous and/or non-aqueous component. The invention also relates to a monolithic implant as thereby manufactured, and the use of such an implant as a scaffold for tissue-engineering and as a transplant tissue in reconstructive or replacement surgery.

14 Claims, 8 Drawing Sheets

Prior Art

IMPLANT FOR TISSUE ENGINEERING

This application is a National Phase filing of International Application No. PCT/GB2007/001520, filed Apr. 25, 2007, which claims priority to GB Patent Application No. 0608345.5, filed Apr. 27, 2006.

FIELD OF THE INVENTION

This invention relates to a process for producing implant materials for use in tissue engineering applications and the implants therein produced.

BACKGROUND TO THE INVENTION

The human skeleton has a number of functions: it protects internal organs, provides muscle attachment sites to facilitate limb movement, acts as a store for calcium and phosphorus, and in some instances produces red blood cells[1]. The adult skeleton contains some 206 bones[2] any one of these may at some time in an individuals life require reconstruction or replacement.

Tissue engineering is defined as the application of principles and methods of engineering and life sciences toward fundamental understanding and development of biological substitutes to restore, maintain and improve tissue functions. Tissue engineering can be applied to both hard and soft tissues. Hard tissue includes, for instance bone and teeth, whereas soft tissue includes, for instance, organs, blood vessels, muscles, ligaments, tendons, cartilage, and nerves.

Implants used for tissue engineering ideally have the following characteristics;
- They are biocompatible; that is, they can function in the body without creating either a local or a systemic rejection response.
- They have mechanical properties that duplicate the structures they are intended to replace; for example, they are strong enough to take weightbearing loads, flexible enough to bear stress without breaking and able to move smoothly against each other as required.

Bone is highly vascular i.e. it contains a network of blood vessels that support rapid healing when required. A problem arises when defects reach a certain size at which point the bone is unable to heal itself. This is known as a critical sized defect, the size at which a defect becomes critical will depend on the age and health of the individual. Such defects may arise as a result of trauma, disease, genetic abnormality, infection, tumour growth or degenerative disease (for example osteoarthritis).

Figure 1:
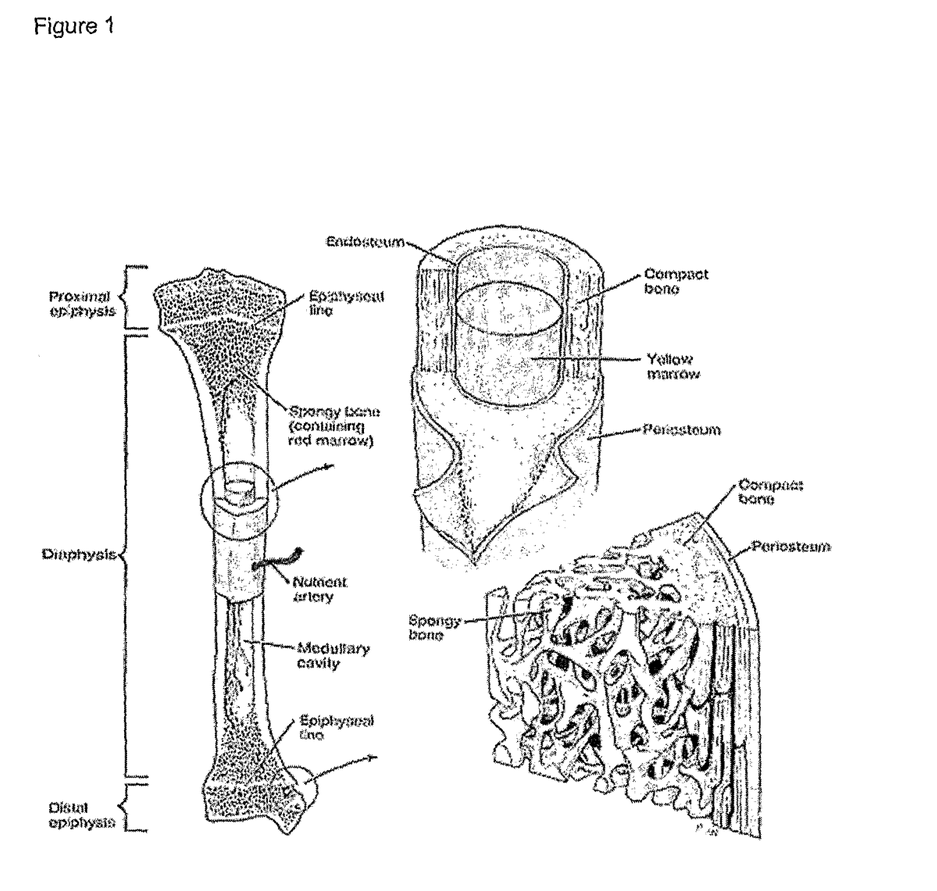
FIG. 1 shows cortical (compact) and trabecular (spongy) bone in the femur.

In relation to the manufacture of a bone implant there is also a serious disconnect between the desire for porosity and strength, since these physical characteristics are mutually exclusive. Bone is a biological composite, it consists of collagen (a fibrous protein) and crystals of hydroxyapatite (HA), a ceramic. The collagen confers flexibility and fracture toughness to the matrix, whilst hydroxyapatite confers stiffness. There are two different types of bone in the skeleton: cortical bone and trabecular bone as illustrated in the femur shown in FIG. 1. These two types of bone which, whilst comprising the same types of cells and material, differ in their structure and how much of the tissue is calcified. Overall cortical bone makes up about 80% of the skeleton, and trabecular bone about 20%, but the proportions of these types of bone differ between different regions of the skeleton.

Cortical bone (also referred to as Haversian bone or compact bone) is a dense calcified tissue (80-90% of the volume is calcified) that forms the outer surfaces of most bones and the shafts of the long bones. It has a low surface area to mass ratio and gives strength and structure to the skeleton and has a Young's modulus of approximately 20 Gpa.

Cancellous bone (also referred to as spongy or trabecular bone) is made up of a network of trabeculae (strands of bone), giving it a characteristic spongy appearance. It has a high surface area to mass ratio and is found mainly at the ends of long bones and in the spine and hip. Only 15-25% of the volume is calcified, the rest of the space is occupied by blood vessels, connective tissue and bone marrow and trabecular has a Young's modulus of only 2 GPa. The main function of trabecular bone is metabolism and is where most bone turnover occurs.

Cortical bone always surrounds cancellous bone although the amount of each varies according to anatomical location. A preferred bone implant replicates the removed bone section in terms of its cortical and trabecular bone geometry.

A range of existing techniques for bone augmentation are currently in use and the basis of these techniques and their inherent advantages and disadvantages are summarized below and in Table 1.

Autografting is the current 'gold standard'. Autografting is the use of bone from one part of a patient's body for use somewhere else. Bone is typically removed from the iliac crest and then used as required [4].

Allografting is a method that uses bone donated from another human. Typically organ donor's bones are removed post mortem and stored in a bone bank ready for use when a surgeon requires it.

Xenografting is a method in which tissue is harvested from another species and therefore all cells and proteins are removed during processing to prevent an immune response.

Bone Cement can be mixed in the operating theatre and moulded to fit the defect in-situ. After mixing the cement hardens rapidly. Historically PMMA (polymethylmethacrylate) cement was used. This is a two part cement that has been used extensively for hip replacement operations over the past 50 years. However, calcium phosphate and calcium sulphate cements are now being used which are more biocompatible and some are biodegradable.

Biocompatible implants are implants fabricated from materials that have minimal effect on the patient. They may be made of plastic or metal fabricated in-situ by the surgeon or made prior to the operation with rapid prototyping techniques [5].

Coralline is coral harvested from reefs and treated to remove any pathogens. Its structure and make up are very similar to native bone such that it promotes in-growth of bone after implantation and is gradually degraded by the body to be replaced by natural bone [6].

Synthetic bone grafts may be made of ceramics, polymers, or a composite of both. Their properties may vary in terms of mechanical strength, porosity, degradation time, and form.

TABLE 1

A summary of the available methods for repairing critical sized bone defects:

| Graft Material | ADVANTAGES | DISADVANTAGES |
| --- | --- | --- |
| Autograft | Contains the patient's own cells<br>Osteoinductive<br>Cortical bone available for strength<br>Resorbable. | Limited amount available<br>Donor site morbidity<br>Increased operative time due to second procedure and hence high cost. |
| Allograft | Off the shelf availability(bone bank)<br>Excellent osteoconductive properties<br>Ideal mechanical properties<br>Resorbable | Processing removes live cells<br>Possibility of infection<br>Implant quality is variable<br>Irradiation can effect properties<br>Limited availability and high cost. |
| Bone Cement (PMMA) | Easily mouldable to fit.<br>Readily available.<br>Can be injected minimally invasively. | High temperature during cure kills cells<br>Unmixed monomer kills cells<br>Non resorbable. |
| Bone Cement (Calcium based) | Easily mouldable to fit.<br>Readily available.<br>Can be injected minimally invasively. Resorbable | Limited porosity<br>Limited strength |
| Biocompatible implants (e.g plastic or metal) | Ideal fit<br>Biocompatible<br>High strength | Allergic reactions to material<br>High cost of preparing implant<br>Non resorbable |
| Coralline Synthetic graft (e.g ceramics, polymers, or a composite of both) | Excellent osteoconductive properties<br>Resorbable<br>Off the shelf availability<br>A multitude of forms available<br>Resorbable<br>No risk of infection | High Cost<br>Poor mechanical properties<br>Limited mechanical properties<br>Moderate cost.<br>Incomplete resorbtion.<br>Properties vary in terms of mechanical strength, porosity, degradation time, form |

An ideal synthetic bone implant would incorporate a number of the advantages of the known techniques without any of the associated disadvantages.

There are two main processes used within the field of bone implant manufacture, referred to as (i) rapid prototyping (RP) or (ii) conventional methods which cover those other than RP (e.g. injection molding).

Figure 2:
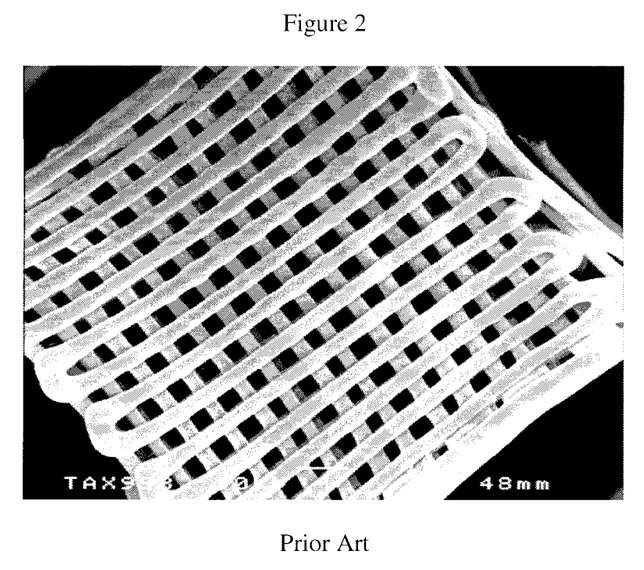
FIG. 2 shows an example of a prior art hydroxyapatite lattice, demonstrating fused deposition of ceramic where a ceramic paste is laid down in a layer by layer to create a porous ceramic artefact (de Sousa, F. C. Gomes and Evans, J. R. G. Tubular hydroxyapatite scaffolds. Advances in Applied Ceramics 104(1), 30-34(5). 2005)

RP refers to a broad category of techniques that can automatically construct physical prototypes from computer-aided design (CAD) models. Rapid prototyping provides the unique opportunity to quickly create functional prototypes of highly complex designs in an additive fashion. This layered manufacturing is also known as solid freeform fabrication (SFF), desktop manufacturing, and computer-aided manufacturing (CAM). There are several methods of RP, but universal to all of them is the basic approach they use, which can be described in three phases; (i) a geometric model is constructed on a CAD/CAM system, (ii) the CAD model is converted into a stereolithograph (STL) and (iii) a computer program reads the generated STL file and slices the model into a finite set of layered cross-sections, each layer then being created individually from liquid, powder, or solid material and stacked onto the previous layer with each layer joined to its neighboring surfaces Fused deposition of ceramic (FDC) is an example of an RP technique in which a thin strand of material is deposited from a needle onto a moving work piece in order to produce a structure as shown in FIG. 2. Hydroxyapatite (HA) scaffolds can be produced using this method by first preparing a paste of HA, propan-2-ol, polyethylene glycol, and polyvinyl butyral in different ratios and drying to the desired consistency[3] The polymer is completely dissolved in solvent before the addition of ceramic powder to the solution. The mixture is then allowed to dry in an oven at 60° C. for approximately one hour with stirring every 10 minutes with the resulting paste being loaded into a syringe and extruded through a polished hypodermic needle onto the moving work piece. Once the scaffold has been completed it is dried in air at 300° C. followed by sintering at 1250° C.

A particular disadvantage of this technique is that the pastes extruded from milled powder could not be extruded easily and produced irregular filaments that curl on exit from the nozzle. Whilst this problem can be overcome by using ultrasonic dispersion, the mix still requires constant stirring.

Whilst RP techniques enable the creation of complex patient specific geometries in a range of different materials, these techniques suffer from many drawbacks, such as: the machines themselves are expensive; the machines are slow to produce scaffolds; the scaffolds require significant post-processing. Above all RP techniques lack scalability. By this it is meant that they cannot produce high volumes of parts at low cost.

All modern car exhausts include a catalytic convertor. This reduces harmful emissions of hydrocarbons, carbon monoxide and nitrogen oxides into the atmosphere. The catalytic convertor works by converting gases into water vapour and less harmful gases.

An automotive catalyst comprises a high specific surface area substrate, typically ceramic or metal, onto which an active (catalytic) wash-coat is added. The wash-coat is designed to further increase the specific surface area and make as much of the active material as possible available to the exhaust gas to increase the reaction rate. The core of the catalytic converter is typicallly a honeycomb cellular monolithic ceramic substrate with pores that measure less than $1/1000$ metre. The pores are coated with a washcoat that contain metals such as platinum, palladium and rhodium.

The preparation of ceramic monoliths from a mixture of cordierite powder and agglomeration agent (e.g. polyethylene oxide or cellulose) for catalyst applications is a well established process.

Surprisingly it has been found that monolithic structures for use as implants in tissue engineering can be manufactured using a similar extrusion process as for the ceramic automotive catalysts.

An object of the invention is to provide an implant for use in tissue engineering which replicates the structure and properties of the natural tissue that it replaces.

An object of the invention is to provide an implant comprising functionally gradient materials.

An object of the invention is to improve the manufacturing process such that the implants can be mass produced in a repeatable, controlled and rapid manner.

BRIEF DESCRIPTION OF THE SEVERAL VIEWS OF THE DRAWINGS

FIG. 7a shows a human mandible, while 7b shows an example of a corresponding extrusion, shaped to have a suitable geometry to match the patient.

STATEMENT OF THE INVENTION

According to a first aspect of the invention there is provided a process for the production of a monolithic implant for use in tissue engineering, said process comprising the steps of;
i) plasticising at least one biocompatible material into a paste;
ii) extruding the paste through a die;
iii) drying the extruded material to eliminate an aqueous and/or non-aqueous component.

Figure 3:
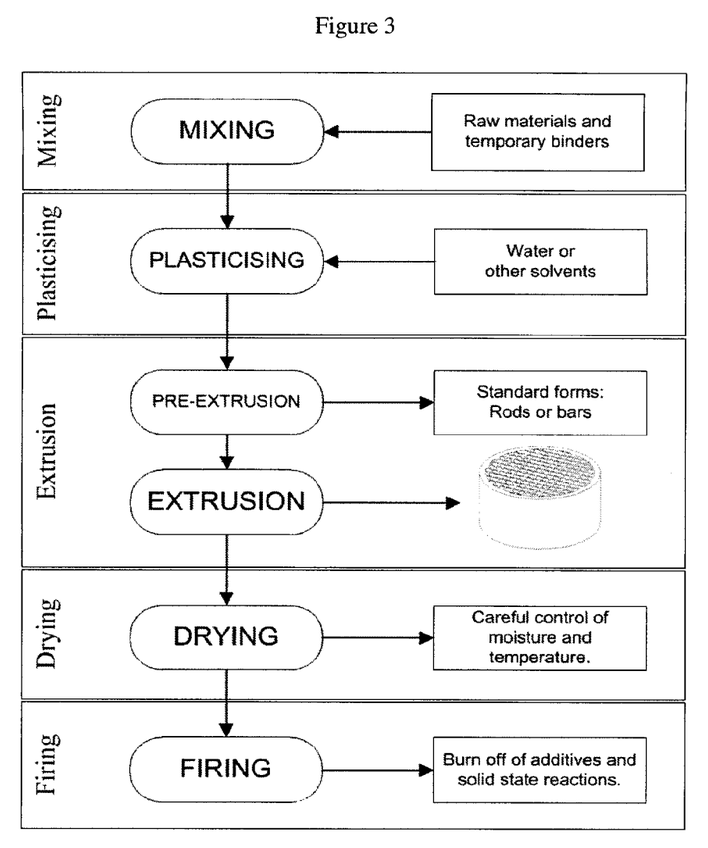
FIG. 3 shows a process for the production of a monolithic implant of the present invention.

The preparation of ceramic monoliths for catalyst applications is a well established process involving the following principal steps: (i) mixing of the raw oxides in order to allow complete reaction during heating, (ii) plasticising, (iii) extrusion of the paste, (iv) drying and (v) firing to transform the raw materials into a monolith. This process is illustrated in FIG. 3.

i) Mixing

Solid powders are combined and dry mixed to ensure a uniform distribution of each of the components in the mix. Extrusion aids, binders, and other fillers are optionally added at this stage which is often simpler than adding these highly viscous materials during the wet mixing stage.

ii) Plasticising

Plasticising or wet mixing follows and continues until the chosen liquid is distributed evenly within the paste. The aim is to cover each solid particle with a film of liquid. As the liquid is incorporated through the powder, a paste with high viscosity develops. This is important since it allows the transfer of high shear forces through the paste which gives rise to uniform packing of the particles and hence stable extrusion. The geometry of the kneading chamber and blades are important factors in this stage, as is the liquid concentration of the paste which needs to be carefully controlled. If the viscosity is too high the mixing of the paste may not be complete. Ceramic pastes are non-Newtonian pseudoplastic fluids and their rheological properties need to be carefully controlled in order to produce high quality extrusions.

In the case of automotive catalysts this stage involves cordierite powder mixed with water and an agglomeration agent e.g. polyethylene oxide or cellulose. The rheological properties and particularly the plastic strength $P_m$, plastic viscosity $\eta_m$, and dynamic limit of catalyst paste fluidity $P_{k2}$ have a significant effect on the extrusion process and the resulting solid. During the kneading process it is also important to account for the electrical properties of the particle surfaces, particularly the isoelectric point (IEP), the zero point charge (ZPC), and the pH of the mixture [8].

Organic additives can be used for a number of reasons; to lower the viscosity of the paste, to act as binders, and for lubrication which is important in the extrusion stage. The nature and content of these additives will have an effect on the morphology of the final product. Methyl-hydroxy-ethyl-cellulose (MHEC) is used as a binder and acts by lowering paste viscosity and improving the compaction of solid particles in the paste. MHEC is soluble in water and reduces the surface tension of the resulting solution thereby improving the wetting of the powder particles. Poly-ethylene-glycol (PEG) is used primarily as a lubricant which has the effect of reducing the pressure required for extrusion and improving the material velocity profile across the die. Too high a concentration of organic fillers leads to a highly porous structure with little mechanical strength. Inorganic additions such as clay and glass fibres can also be used as binders but their main use is to increase the mechanical strength of the final product [7].

Additional materials can be added to either improve macro porosity (saw dust, starch) or improve mechanical properties (mullite, zirconia). Other treatments are also possible in order to aid the extrusion of the paste, prevent cracking, increase surface area, or reduce thermal expansion. Control of raw material particle size is also important to achieve good contact between the components of the reaction.

iii) Extrusion

Figure 4:
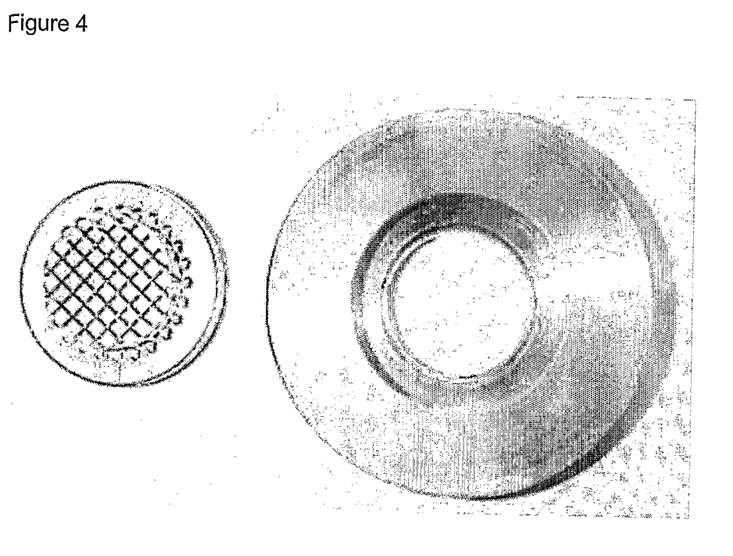
FIG. 4 shows an example of an extrusion die which may be used during the extrusion phase of the process of the present invention.

The resulting paste is extruded through a series of dies. The first of which results in the extrusion of a simple rod form. The ceramic paste is forced through the die by means of a screw extruder or ram. A screw extruder is better suited to continuous production than a ram. The resulting cross section of the extrudate closely matches the die. This extruded rod will then be fed through the final die by a ram. A typical example of the final extrusion die is shown in FIG. 4.

Figure 5:
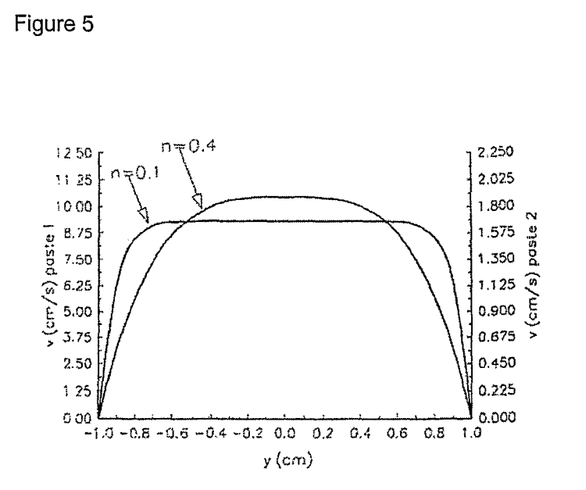
FIG. 5 shows a comparison of material velocity profiles during the extrusion phase. The desirable profile (n=0.1, paste 2) is flat in nature with a rapid decrease in velocity at the walls of the extruder. A poor velocity profile (n=0.4, paste 1) is more curved and can be characteristic of a paste which has dried out too much around the periphery.

The extrusion process is sensitive to many factors one of which is the material velocity profile across the tool. FIG. 5 displays two curves one of which is a desirable velocity profile the other undesirable. The desirable profile (n=0.1, paste 2) is flat in nature with a rapid decrease in velocity at the walls of the extruder. A poor velocity profile (n=0.4, paste 1) is more curved and can be characteristic of a paste which has dried out too much around the periphery.

iv) Drying

The 'green' component is air dried at 30-100° C. The drying phase is an important part of the process where the water is eliminated from the green part resulting in shrinkage. This is where cracks may form that can be large enough to break the monolith. The temperature and humidity of this process must be controlled carefully to dry out the monolith slowly and uniformly to achieve high compaction with no cracking.

v) Firing

Firing is the final step in the production of the monolith and must be controlled carefully in order to prevent cracking. The first step is to carry out a differential thermal analysis-thermogravimetry (DTA-TG) analysis of the paste to determine at what temperatures the exothermic burn off of additives occurs. During this burn off phase the heating rate and air flow need to be controlled to avoid hot spots on the monolith. The final firing temperature for the monolith is dependant upon the material being used but it is typically calcined at 1300-1400° C. for 3-4 hours.

Throughout the description and the claims of this specification, the words "comprise" and "contain" and variations of the words, for example, "comprising" and "comprises", means "including but not limited to" and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

In a further embodiment of the invention the process additionally comprises the step of firing the dried monolithic implant at typical temperatures of, for example, 1300-1400° C. for 3-4 hours.

Biocompatible Materials

A biocompatible material has the property of being biologically compatible by not producing a toxic, injurious, or immunological response in living tissue. In preferred embodiments of the invention, the biocompatible material is selected from the following classes of material; ceramic, glass or glass ceramic.

Examples of suitable ceramic, glass or glass-ceramic materials are listed in Tables 2, 3 and 4, respectively.

TABLE 2

Ceramic materials
Ceramics

Amorphous Calcium Phosphate (ACP)
Ascorbate-2-phosphate (AsAP)
Calcium Phosphate Cement (CPC)
Hydroxycarbonate apatite (HCA)
Hydroxyapatite (HA)
Tri-Calcium Phosphate (TCP)
Aluminium calcium phosphorus oxides
Zinc sulphate calcium phosphorus oxides
Ferric calcium phosphorus oxide
Corals
Zinc calcium phosphorus oxides TABLE 2-continued Ceramic materials
Ceramics Alumina based including stabilised ceramics
Zirconia based including stabilised ceramics The above ceramics with various degrees of cationic and anionic substitutions

TABLE 3

Glass materials
Glass

Bioglass ® series including 45S5, 52S4, 42SF, 46SF, 49SF, 52SF, 55SF, 60SF, 49S, 54S, 58S, 63S, 68S, 72S, 77S, 86S and the variation of these compositions
Ceravital ® based compositions

TABLE 4

Glass-ceramic materials
Glass ceramics

Bioglass ® based multiphase glass-ceramics
Apatite based multi-phase glass-ceramics
Wallstonite based multi-phase glass-ceramics
Apatite-Wallstonite (A/W) based multiphase glass-ceramics
Machinable phosphosilicates and variations thereof and mica and apatite phase based glass-ceramics
Phlogopite In an alternative embodiment of the invention the biocompatible material is a polymer. Examples of suitable synthetic polymers are listed in Table 5. Preferably the synthetic polymer is an alpha-polyester, such as a polylactide or polyglycolide because the breakdown products of these two materials, lactic acid and glycolic acid respectively are familiar to the physiological milieu of the body. Alternatively the polymer is a natural polymer, for example, collagen, chitin, chitosan and elastin.

TABLE 5

Synthetic Polymers
Polymers

Poly(anhydride) (PA)
poly lactic acid (PLA)
poly glycolic acid (PGA)
poly(L-lactide) (PLLA)
poly(L-lactide-co-glycolide) (PLGA)
poly(D,L-lactide) (PDLLA)
poly(L-Lactide-co-DL-lactide) (PLDL)
Poly(lactide-co-glycolide) (PLAGA)
poly(D,L-lactide-co-glycolide) (PDLGA)
polycaprolactone (PCL)
poly(ε-caprolactone (CL)-DL-lactide (LA)) tetraacrylate (PCLLA)
poly(apidic acid-co-octanediol-co-sorbitol) (PAOS)
poly(butylene terephthalate) (PBT)
hydrophobic polybutylene terephthalate (PBT)
methylmethacrylate (MMA)
Polymethylmethacrylate (PMMA)
n-butylmethacrylate (nBMA)
Polyetheretherketone (PEEK)
Polyethylene glycol (PEG)
poly(ethylene glycol terephthalate) (PEGT)
polyoxyethylenelaurylether (PEI)
poly ethylene oxide (PEO)
Poly(ortho ester) (POE)
Polypropylene (PP)
poly(p-dioxanone-co-L-lactide)-block-Poly(ethylene glycol)
PPDO/PLLA-b-PEG
Poly Propylene Fumarate (PPF)

TABLE 5-continued

Synthetic Polymers
Polymers

Poly (propylene fumarate)-diacrylate (PPF-DA)
Polyurethane (PU)
Poly Vinyl Alcohol (PVA)
Poly(1-vinyl pyrrolidone) (PVP)
Starch/cellulose acetate (SCA)
Starch/Ethylene Vinyl Alchohol (SEVA-C)
Polyhydroxyalkanoate (PHA)
poly(2-hydroxyethyl methacrylate) (PHEMA)
Hydroxyethyl methacrylate (HEMA)

Other materials which can be used as constituents of the monolithic implant include, for example hydrogels or demineralised bone matrix (DBM).

In further embodiments of the invention, the implant comprises at least two biocompatible materials, thereby combining the physical and chemical properties of both materials.

In further embodiments of the invention, the plasticized paste contains a homogenous mixture of at least two biocompatible materials. The ratio of the mix of the two materials within the paste is variable, thereby enabling the physical and chemical properties of the monolithic implant to be varied according to requirements.

In further embodiments of the invention, the plasticized paste contains layers of at least two biocompatible materials. For example, the paste contains a polymer core which is surrounded by a ceramic coating.

In further embodiments of the invention, a second biocompatible material is dispersed within a first biocompatible material. For example, particles of a polymer are dispersed throughout a plasticized ceramic paste. Due to the fact that the polymer has a lower melting point than the ceramic, it is "burned off" during the firing of the ceramic, leaving behind a porous structure.

There are three ways that a bone graft can help repair a defect;
  Osteogenesis, the formation of new bone by the cells contained within the graft.
  Osteoinduction, a chemical process in which molecules contained within the graft (e.g bone morphogenetic proteins) convert the patient's cells into cells capable of forming bone.
  Osteoconduction, a physical effect whereby the graft matrix configures a scaffold on which cells in the recipient form new bone.

In a further preferred embodiment of the invention the monolithic implant comprises any combination of biocompatible materials that includes an osteoconductive matrix, an osteogenic material and an osteoinductive material, therefore fulfilling the three requirements for a successful bone graft.

Functionally gradient materials (FGMs) or anisotropic materials provide a solution where two or more materials with distinct properties are required to be put together. These materials can accommodate a gradual transition of the properties of different materials from one side to the other where the mismatch in properties, such as mechanical and thermal properties, is reduced to a minimum. In further preferred embodiments of the invention the monolithic implant is a FGM.

Implant Resorption

The resorptive capacity of an implant is principally dependent on its chemical composition. Conventionally implants are classified as being substantially inert, partially resorbable or totally resorbable.

The resorptive capacity of an implant is chosen to meet the requirements of a particular anatomical site. For example, an open edge osteotomy is preferably substantially biodegradable and degrades at the rate that the new structural bone is laid down.

Therefore, in preferred embodiments of the invention the implant is substantially inert. In alternative embodiments of the invention the implant is partially or totally resorbable. The rate of resorption of the implant is controlled by the selection of the biomaterial(s) used.

Implant Porosity

Implant porosity has a significant influence on both the physical and chemical interactions between the implant and the surrounding tissue. Porosity increases the available surface area for cellular interactions, effecting for instance mechanical integration of the implant at the implantation site and also the rate of implant resorption. Materials with little or no porosity do not allow cellular penetration.

Preferably the porosity of the implant replicates the natural tissue. For example in a segmental bone defect a highly porous central section (mimicking trabecular bone) would be surrounded by a stronger, and less porous external shell (mimicking cortical bone) to provide some structural support.

In preferred embodiments of the invention, the implant is a simple, regular, porous structure of open structure with large channels (0.5-2 mm) since this performs better than foam type structures in vivo due to better blood transport, thus meeting the nutrient requirements of the cells residing within the implant.

The morphology, modality and/or distribution of the pores can be varied depending on the implant requirements. The pores can be uni- or multidirectional.

The monolithic implant for use as a bone implant preferably comprises at least one of following types of porosity:
  Macroporosity (100-1000 μm) allows new bone to grow in apposition implant surfaces throughout the implant.
  Interconnecting meso (0.02-0.05 μm) and microporosity (<10 μm) permits fluid communication and nutrient transport to support bone regrowth throughout the implant.
  Nano particle size (<1 nm) construction facilitates cell-mediated implant resorption.

In an embodiment of the invention the pores are formed during extrusion of the paste through the die(s). Further pores can be created post-extrusion using a laser, and such techniques are known to those skilled in the art.

In further embodiments of the invention additional materials, for example saw dust or starch, are added to the pliable material prior to extrusion in order to improve macroporosity.

Figure 6:
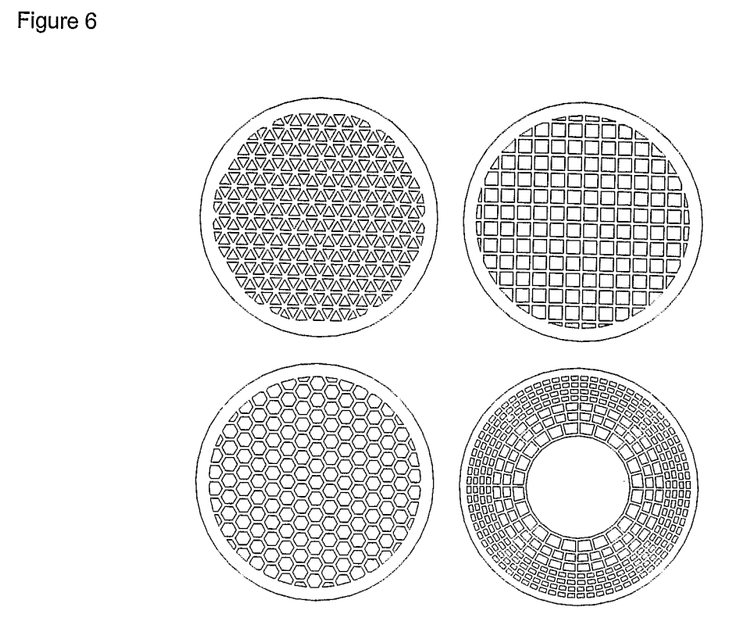
FIG. 6 shows a range of monoliths that may be extruded where the channels are formed of polygons with any number of sides, for example: three sides (triangular), four sides (square) or six sides (hexagonal).

In preferred embodiment of the invention the monolith is composed of a series of repeating polygons that combine to form the structure: Polygons are defined as being a closed plane figure bounded by three or more line segments. The polygonal units forming the monolith can vary in size and shape as illustrated in FIG. 6. The polygonal units may be, for example, triangular, square, or hexagonal. In an embodiment of the invention the monolith consists of a plurality of polygonal units of the same shape. In an alternative embodiment of the invention the monolith consists of a plurality of polygonal units of at least two different shapes.

For example, a plasticized material can be extruded through a die assembly such that the end product comprises a functionally gradient pore structure.

Bioactive Implant

The surface of an implant determines its ultimate ability to integrate into the surrounding tissue. The composite effect of surface energy, composition, roughness, and topography plays a major role during the initial phases of the biological response to the implant, such as protein adsorption and cellular adherence, as well as during the later and more chronic phases of the response[13]. In the case of osteointegration, if the implant surface is inappropriate or less than optimal, cells will be unable to produce the appropriate complement of autocrine and paracrine factors required for adequate stimulation of osteogenesis at the implant site. In contrast, if the surface is appropriate, cells at the implant surface will stimulate interactions between cells at the surface and those in distal tissues. This, in turn, will initiate a timely sequence of events which include cell proliferation, differentiation, matrix synthesis, and local factor production, thereby resulting in the successful incorporation of the implant into the surrounding bony tissue.

It has been demonstrated that the extent of bone-implant interface is positively correlated with an increasing roughness of the implant surface. Sandblasted and acid (HCl/H2SO4)—attacked surfaces exhibit a high extent of bone-implant interface[14].

Therefore, in an embodiment of the invention, at least part of the surface of the implant is rough.

A hydrophilic surface will quickly attract blood and serum to the implant surface, therefore facilitating the movement of cells and other components, for example, growth factors (e.g TGF) into the network of pores within the implant.

Therefore in an embodiment of the invention, at least part of the surface of the implant is hydrophilic.

Bone is under a constant process remodeling, defined by the process of resorption and formation. Bone resorption is the unique function of the osteoclast. Bone regeneration is the unique function of the osteoblast.

Bone resorption has been identified in ceramic implants and appears to involve two different cell types. Acid phosphatase-positive osteoclast-like cells suggesting active resorption adhere directly to the surface, especially in tricalcium phosphate implants. Additionally clusters of macrophages tightly packed with granular material are found in the pores and along the perimeter of all implant cylinders, suggesting that they may play an active role in the intracellular degradation of small detached ceramic particles.

The rate of regeneration of tissue around an implant may be improved by supplementing the implant with an appropriate cell type, with resorptive and/or regenerative capabilities.

In a preferred embodiment of the invention the cell is a regeneration competent cell, such as a stem cell derived from an embryo, fetus or adult.

In an embodiment of the invention the stem cell is totipotent. A totipotent cell is taken from a 4-8 cell stage of a fertilized embryo and has the potential to divide and develop into a human being.

In an embodiment of the invention the stem cell is pluripotent. A pluripotent cell is taken from embryonic/foetal tissue and has the potential to form any type of cell, but not an entire human being.

In an embodiment of the invention the stem cell is multipotent. A multipotent cell can only differentiate into a limited range of cell types.

In an embodiment of the invention the cell is a bone generating cell. For example an osteoblast or osteoblast-like cell.

The cell may be seeded into the porous network of the monolithic implant or alternatively attached, by any method known to one skilled in the art, to a surface of the implant.

Problems can arise from the lack of osteo-integration of the implants within the bone. Small gaps between the implant and the bone are open for particles or bacteria, which leads to a chronic inflammatory response, bone resorption and the subsequent mechanical failure of the implant. One way to improve the integration of the implant into the bone is to encourage bone growth to the implant surface by covering it with a biocompatible and bioactive film. A preferable coating significantly increases implant surface area and mechanical retention in the bone at the time of placement and has numerous asperities on the surface which allow an improvement in osseointegration and interlock. The direct adhesion of osteoblasts to this film closes the gap between bone and implant early after implantation, therefore improving integration and minimalising infection. Examples of these films include bioactive polymers or bioactive calcium phosphate coatings.

In a further embodiment of the invention, the monolithic implant comprising a bioactive coating/film.

Geometric Shapes of Monolithic Implants

Figure 7A:
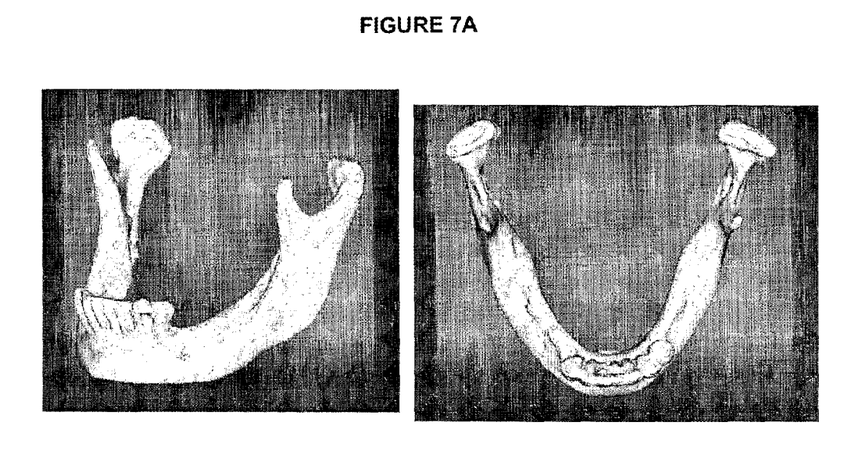
Figure 7B:
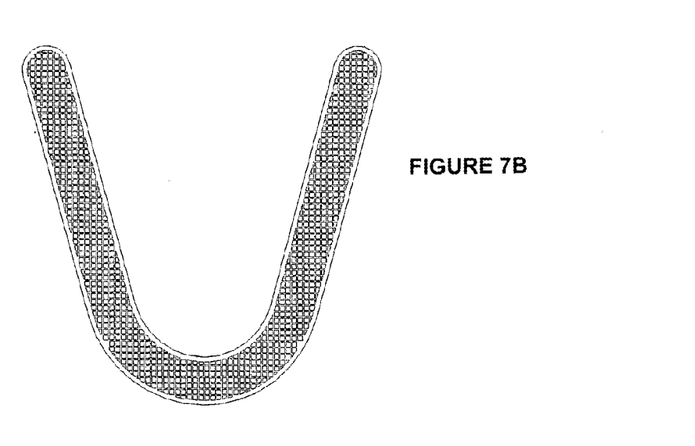
Figure 8:
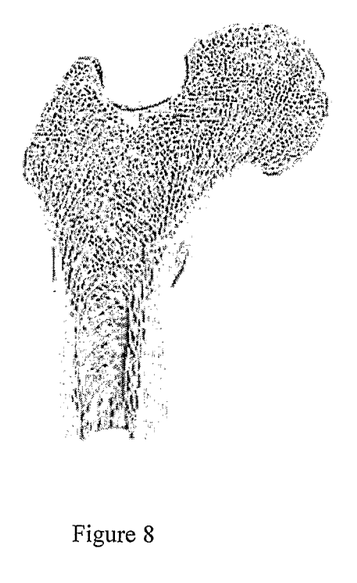
FIG. 8 shows a cross-section of a human hip with the alignment of trabecular bone visible.

As well as extrusion of monolithic cylinders it is also possible to make many other geometric shapes. The extrusion of the pliable material through an appropriately shaped die enables the manufacture of a monolithic implant with optimised geometry to mimic the natural organs. For example to create a replacement for a human mandible (FIG. 7a) it would be possible to extrude a form that closely resembles the plan view of it. This extrusion could then be trimmed by the surgeon or for a closer match, machined to suit. FIG. 7b demonstrates how the extrusion might look. For example, in the manufacture of a replacement hip, the monolith is extruded in the form of a curve in order to align the internal structure of the monolith with the lines of stress within the hip itself as found to occur naturally. FIG. 8 shows a cross section of a human hip with the alignment of trabecular bone visible.

Tissue Engineering Scaffolds

Extrusion of monolithic structures can be applied to tissue engineering scaffolds for other organs, apart from bone. The scaffold properties can be tailored for any particular tissue engineering application. For example in lung tissue engineering the scaffold would have to be highly flexible to cope with the constant movement of the chest, as well as conducive to the growth of lung cells. A flexible polymer or hydrogel would be most suited to this application. The scaffold may also need an outer skin of a different material that allows the implant to be sutured to the existing lung tissue as well as providing an air tight seal. The pore size and overall porosity of the monolith as well the material surface properties could be tailored to suit the cells likely to populate the scaffold.

Other examples of tissue engineered organs may be for the liver or kidneys. These would have less need for flexibility and so a degradable polymer would be a suitable material. Again the scaffold porosity and surface properties would have to be optimised to suit the relevant cells. Another possible application is in the manufacture of synthetic skin. Materials currently used for skin could be extruded into strips of porous material that could help repair multiple layers of skin Therefore, in an embodiment of the invention, the monolithic implant is a soft-tissue implant. Soft tissue implants are conventionally used for the following purposes: to reconstruct surgically or traumatically created tissue voids, to restore bulk to aging tissues in order to correct soft tissue folds or rhytides or to augment tissue for cosmetic enhancement. Soft tissue implants include, for instance, organ, blood vessel, muscle, ligament, tendon, cartilage or nerve implants.

In an embodiment of the invention, the monolithic implant is a hard-tissue implant, for example a bone or dental implant. Preferably the monolithic implant is an orthopaedic implant.

According to a further aspect of the invention there is provided an implant manufactured according to the process of the present invention.

According to a further aspect of the invention there is provided use of a monolithic implant produced by the method of the invention as a scaffold for tissue engineering.

According to a further aspect of the invention there is provided use of a monolithic implant produced by the method of the invention as a transplant tissue in reconstructive or replacement surgery.

REFERENCES

1. Margareta Nordin and Victor H. Frankel. Basic Biomechanics of the Musculoskeletal system. 89. USA, Williams & Wilkins. 89.
2. Alexander P. Spence. Basic Medical Anatomy. 82. Benjamin-Cummings. 82.
3. de Sousa, F. C. Gomes and Evans, J. R. G. Tubular hydroxyapatite scaffolds. Advances in Applied Ceramics 104(1), 30-34(5). 2005.
3. B. D. Porter, J. B. Oldham, S.-L. He, and M. E. Zobitz. Mechanical Properties of a Biodegradable Bone Regeneration Scaffold. Journal of Biomechanical Engineering 122 (3), 286-288. 2000. American Society of Mechanical Engineers.
4. E. M. Erbe, J. G. Marx, T. D. Clineff, L. D. Bellincampi, *Eur Spine J* 10 Suppl 2, S141-6 (2001).
5. Liu Yaxiong, Li Dichen, Lu Bingheng, He Sanhu, and Li Gang. The customized mandible substitute based on rapid prototyping. Rapid Prototyping Journal 9(3), 167-174. 2003. Emerald Group Publishing Ltd.
6. H. Petite et al., *Nat Biotechnol* 18, 959-63 (2000).
7. Forzatti, Pio, Ballardini, Daniele, and Sighicelli, Lorenzo. Preparation and characterization of extruded monolithic ceramic catalysts. Catalysis Today 41(1-3), 87-94. 98.
8. Avila, Pedro, Montes, Mario, and Miro, Eduardo E. Monolithic reactors for environmental applications: A review on preparation technologies. Chemical Engineering Journal 109(1-3), 11-36. 2005.
9. Laboratory of Environmental Catalys. Monolithic honeycomb supports and catalysts. 2006.
11. Family Doctor. Sample Chapter—understanding osteoporosis. 2006.
12. Medical Art Service. Cross-section of Femur BA 216. 2006.
13. Kieswetter K, Schwartz Z, Dean D D, Boyan B D. The role of implant surface characteristics in the healing of bone. *Crit Rev Oral Biol Med.* 1996; 7(4):329-45.
14. Buser D, Schenk R K, Steinemann S, Fiorellini J P, Fox C H, Stich H. Influence of surface characteristics on bone integration of titanium implants. A histomorphometric study in miniature pigs. J Biomed Mater Res. 1991 July; 25(7):889-902.

The invention claimed is:

1. A method of producing a monolithic implant for use in tissue engineering, the implant having a structure comprising channels of 0.5-2 mm width and further comprising at least one porous region each having porosity in the range 100-1000 µm or less than 10 µm, said method comprising the steps of:
   i) plasticising at least one biocompatible material into a paste in water;
   ii) extruding the paste through a die being so dimensioned to impart said channel structure to the extruded material;
   iii) drying the extruded material to eliminate an aqueous and/or non-aqueous component; and
   iv) firing the dried extruded material to form said monolithic implant,
   wherein the paste in step (i) is made up from a first biocompatible material having a second biocompatible material dispersed within it.

2. The method according to claim 1, wherein the first biocompatible material is a plasticized ceramic paste and the second biocompatible material is a polymer.

3. The method according to claim 2, wherein the ceramic is hydroxyapatite.

4. The method according to claim 1, wherein the monolithic implant consists of a plurality of polygonal units of at least two different shapes.

5. The method according to claim 1, wherein at least part of a surface of the monolithic implant is adapted to promote cell attraction.

6. The method according to claim 1, wherein the implant is supplemented with a cell type.

7. The method according to claim 1 wherein the monolith comprises a hydrogel or demineralised bone matrix (DBM).

8. A method of producing a monolithic implant for use in tissue engineering comprising:
   i) plasticising at least one biocompatible material into a paste in water, wherein the biocompatible material comprises a first biocompatible material having a second biocompatible material dispersed within it;
   ii) extruding the paste through a die being so dimensioned to impart a channel structure to the extruded material;
   iii) drying the extruded material to reduce an aqueous and/or non-aqueous component; and
   iv) firing the dried extruded material to form said monolithic implant, wherein the channels imparted by the extrusion step result in channels having a width of 0.5-2 mm after firing, and the monolithic implant further comprises porosity in the range 100-1000 µm or less than 10 µm after firing.

9. The method according to claim 8, wherein the first biocompatible material is a plasticized ceramic paste and the second biocompatible material is a polymer.

10. The method according to claim 9, wherein the ceramic is hydroxyapatite.

11. The method according to claim 8, wherein the monolithic implant comprises a plurality of polygonal units of at least two different shapes.

12. The method according to claim 8, wherein at least part of a surface of the monolithic implant is adapted to promote cell attraction.

13. The method according to claim 8, wherein the implant is supplemented with a cell type.

14. The method according to claim 8, wherein the monolith comprises a hydrogel or demineralised bone matrix (DBM).

* * * * *

UNITED STATES PATENT AND TRADEMARK OFFICE
CERTIFICATE OF CORRECTION

PATENT NO. : 8,623,394 B2  Page 1 of 1
APPLICATION NO. : 12/298618
DATED : January 7, 2014
INVENTOR(S) : Mallick et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1092 days.

Signed and Sealed this
Twenty-second Day of September, 2015

Michelle K. Lee
*Director of the United States Patent and Trademark Office*